United States Patent [19]

Das et al.

[11] Patent Number: 5,401,504

[45] Date of Patent: Mar. 28, 1995

US005401504A

[54] USE OF TURMERIC IN WOUND HEALING

[75] Inventors: Suman K. Das; Hari Har P. Cohly, both of Jackson, Miss.

[73] Assignee: University of Mississippi Medical Center, Jackson, Miss.

[21] Appl. No.: 174,363

[22] Filed: Dec. 28, 1993

[51] Int. Cl.⁶ ............................................. A61K 35/78
[52] U.S. Cl. .................. 424/195.1; 514/925; 514/926; 514/927; 514/928
[58] Field of Search ..................................... 424/195.1

[56] References Cited

U.S. PATENT DOCUMENTS

| | | | |
|---|---|---|---|
| 4,719,111 | 1/1988 | Wilson | 424/195.1 |
| 5,120,538 | 6/1992 | Oei | 424/195.1 |
| 5,252,344 | 10/1993 | Shi | 424/682 |

OTHER PUBLICATIONS

Institute GA. 99: 218620T (1983) of JPN. 58-162520 (Ulcer Inhibitor Tablets Effective in Mice Contain Carcinogen).
Soma et al GA. 116: 221612S (1992) of JPN 4-49240 (Digestive Tract Ulcers Treated with *Curcuma longa* (Turmeric) Extract (Lipopolysaccharides)).
Kumar et al GA.119: 871K (1993) of Ind. Vet. J. 70(1):42-4 (1993).
Abstracts of Charles et al Trop. Geogr. Med: 44(1-2) 178-181 Jan. 1992; Rafatullah et al J. Ethnopharmacol. 29(1): 25-34 Apr. 1990; Kutton et al Tumori 73(1): 29-31 Feb. 28, 1987; Mehra et al. Tokai J Etpharm Med 9(1): 27-31 Mar. 1984.

*Primary Examiner*—Shep K. Rose
*Attorney, Agent, or Firm*—Wenderoth, Lind & Ponack

[57] ABSTRACT

Method of promoting healing of a wound by administering turmeric to a patient afflicted with the wound.

6 Claims, No Drawings

USE OF TURMERIC IN WOUND HEALING

BACKGROUND OF THE INVENTION

The present invention relates to the use of turmeric to augment the healing process of chronic and acute wounds.

The pharmacokinetics involving the safety, toxicity, dose range, and biological properties of turmeric are known, and the agent is readily available in the food store.

The incidence of ulcers in legs is approximately 1% in the adult population, and 3-4% of persons over the age of 65 have a history of these ulcers. These data are derived from the United States and Europe, according to the recent FDA workshop in Washington ("Clinical Trial Issues of Tropical Wound Healing Biologics," Apr. 22-23, 1993). This conference stressed the application of multifactorial growth factors to chronic wounds. Principles underlying the healing of chronic ulcers require control of three local factors: infection, oxygenation, and edema.

The basic process in regard to angiogenesis as it relates to wound healing deals with the capillaries, which consist of endothelial cells and pericytes. These cells do not divide readily but undergo rapid proliferation during spurts of angiogenesis in wound healing. The present inventors have generated experimental evidence showing that turmeric causes endothelial cells to proliferate, indicating that this molecule can be used to augment wound healing.

Turmeric, a yellow powder developed from the plant *Curcuma longa*, is commonly used as a food colorant in many Indian dishes and imparts a bitter taste. Turmeric is also used as an additive in prepared mustard.

Although it is primarily a dietary agent, turmeric has long been used in India as a traditional medicine for the treatment of various sprains and inflammatory conditions (Rao T S et al., *Indian J. Med. Res.*, 75:574–578, 1982). The active ingredient in turmeric powder is curcumin, which is a completely symmetrical molecule (Govindarajan V S., *Crit. Rev. Food Sci. Nutr.*, 12:199–301, 1980). At present, there is no evidence to indicate that habitual consumption of turmeric has any toxic effects in humans and the FAO/WHO has allocated a temporary admissible daily intake of 0-2.5 mg/kg$^3$ (Vijayalaxmi, Mutat. Res., 79:125–132,1980).

Extensive in vitro and in vivo testing has shown that turmeric inhibits chemically-induced epidermal ornithine decarboxylase activity, epidermal DNA synthesis, and the promotion of skin tumors in mice (Conney A H et al., *Adv. Enzyme Regul.*, 31:385–396, 1991; Huang M T et al., *Cancer Res.*, 48:5941–5945, 1988; Lu Y P et al., *Carcinogenesis*, 14:293–297, 1993; Azuine M A, Bhide S V, *Nutr Cancer*, 17:77–83, 1992). Further studies suggest that turmeric also reduces arachidonic acid-induced rat paw and mouse skin edema and markedly inhibits epidermal lipoxygenase and cyclooxygenase activity in vitro (Rao T S et al., *Indian J. Med. Res.*, 75:574–578, 1982; Conney A H et al., *Adv. Enzyme Regul.*, 31:385–396, 1991; Huang M T et al., *Cancer Res.*, 48:5941–5945, 1988). In humans, ingestion of turmeric has demonstrated a bacteriostatic or bacteriocidal effect against organisms involved in cholecystitis and has been used to treat biliary infections (Ramprasad C et al., *Ind. J. Phys. and Pharm.*, 1:136–143, 1957; Lutumski J et al., *Planta Med.*, 26:9–19, 1974). Topical application of a turmeric paste for the treatment of scabies has also shown good results (Charles V, Charles S X., *Trop. Geogr. Med.*, 44:178–181, 1992).

It has been recently shown that curcumin decreased p24 antigen production in acutely or chronically infected cells with HIV-1, a paradigm of anti-viral activity (Li C J et al., *Proc. Natl. Acad. Sci. USA*, 90:1839–1842, 1993). Administration of curcumin in mice significantly reduced the scavenging of peroxides and other activated oxygen species, exhibiting its antioxidant property (Soudamini K K et al., *Indian J. Phys. Pharmacol.* 36:239–243, 1992). Oral administration of curcumin in human volunteers has been shown to significantly decrease the level of serum lipid peroxides (33%), increase HDL cholesterol (29%), and decrease total serum cholesterol (11.63%) (Soni K B, Kuttan R., *Indian J. Phys. Pharmacol.*, 36:273–275, 1992).

The addition of turmeric to diet has been shown to inhibit azoxymethanol-induced colonic epithelial cell proliferation and focal areas of dysplasia (Huang M T et al., *Cancer Letters*, 64:117–121, 1992). It has also been shown to interfere with the formation of covalent carcinogen-DNA adducts (Mukudan M A et al., *Cardnogenesis*, 14:493–496, 1993).

Fat metabolism is likewise influenced by curcumin. It can render bile non-lithogenic in mice (Hussain M S et al., *Indian J. Med. Rcs.*, 96:288–291, 1992). Curcumin can reduce the production of PMA-induced lipid peroxidation and 8-OH-deoxyguanosine formation in mouse fibroblast cells (Shih C-A, and Lin J-K, *Carcinogenesis*, 14:709–712, 1993).

Phosphorylation events can also be influenced by curcumin, as it has been reported that curcumin inhibits protein kinase C activity induced by 12-O-tetradecanoyl-phorbol-13-acetate in NIH 3T3 cells (Liu, J-Y, Lin, S-J, and Lin, J-K., *Carcinogenesis*, 14:857–861).

Curcumin inhibits the immune as well as the smooth muscle cell proliferation. Human peripheral blood mononuclear cells were inhibited in response to phytohemagglutinin and mixed lymphocyte reaction. Furthermore, curcumin inhibited the proliferation of rabbit vascular smooth muscle cells stimulated by fetal calf serum. Curcumin had a greater inhibitory effect on platelet derived growth factor-stimulated proliferation than on serum-stimulated proliferation (Huang H-C et al., *Eur. J. Pharmacol.*, 221:381–384, 1992).

The anti-inflammatory properties of curcumin were shown to inhibit the 5-lipoxygenase activity in rat peritoneal neutrophils as well as the 12-lipoxygenase and the cyclooxygenase activities in human platelets (Ammon H P T et al, *J. Ethopharmacol.*, 38:113–119, 1993). Curcumin had no significant effect on quercetin-induced nuclear DNA damage, lipid peroxidation and protein degradation and thus has the unique potential of acting as both pro- and antioxidants, depending on the redox state of their biological environment (Saura C et al., *Cancer Letters*, 63:237–241, 1992).

SUMMARY OF THE INVENTION

The present invention is directed to the use of turmeric to promote wound healing. The present inventors have found that the use of turmeric at the site of an injury by topical application and/or oral intake of turmeric will promote healing of wounds.

DETAILED DESCRIPTION OF THE INVENTION

The present invention provides a method of promoting healing of a wound in a patient, which comprises administering a wound-healing effective amount of turmeric to the patient.

The present inventors postulated that turmeric may have significant antineoplastic, antioxidant, antibacterial and anti-inflammatory properties when given orally or applied topically. In view of these facts and the availability of turmeric, the present inventors studied the wound healing properties of turmeric to provide a simple and economical solution to the problem of chronic ulcers.

If curcumin is presumed to be the active moiety, its unique property is its axis. of symmetry around the $CH_2$ group (Govindarajan VS., Crit. Rev. Food. Sci. Nutr., 12:199-301, 1980).

It is postulated that turmeric contributes to the treatment of chronic ulcers through the following mechanism: 1) improvement of microcirculation, 2) stimulation of angiogenesis, 3) promotion of granulation tissue formation, and 4) acceleration of reepithelialization.

Some investigators hold that there is no single factor that can address the problem of wound healing. The literature and various conferences stress the use of several growth factors for healing wounds. This multifactorial approach would result in a very high economic burden on an already strained health care system. Also, turmeric is a natural product that is readily available in the food store.

Before entering turmeric into a clinical trial, the powder was tested for its healing ability in acute wounds created by surgical incision. Although a wide variety of animal models are available, the inventors chose to fashion full-thickness circular wounds on rats and allow them to heal by secondary intention. Thus, each wound had to undergo a significant amount of wound contraction, which allowed for easy documentation of decreasing wound size throughout the experiment. Furthermore, by leaving the wounds open, any accelerating or retarding effects that a sterile dressing may have had on the wound were eliminated.

All of the wounds in this study exhibited the typical pattern of wound healing, with minimal wound contraction noted during the initial lag phase followed by a rapid increase in wound contraction during the proliferative phase (day 6 to day 25) (Hayward P G et al., Prog Clin. Biol. Res., 365:301-312, 1991). In the animals treated with local and/or oral turmeric the mean wound sizes were significantly smaller during this proliferative phase when compared to the mean wound size of the animals treated with normal saline. This suggests that local application and oral intake of turmeric may enhance wound contraction when compared to daily cleansing with saline.

Thus, turmeric offers an alternative to conventional therapy for full-thickness wounds. Considering that turmeric is readily available and economical, this could be of particular importance to the indigent population, which suffers significant morbidity from complex wounds.

Growth factor knowledge, the use of animal models, and the body of literature on wounds per se have not conclusively addressed the serious problem of skin ulcers. One report detailed an investigation in which two factors, neem and turmeric, were used to treat scabies in a village in India. This multi-drug approach is more difficult to assess than the single factor approach being used here for humans (Charles V, Charles S X., Trop. Geogr. Med., 44:178-181, 1992). Growth factors, in particular platelet derived growth factor (PDGF) and transforming growth factor-B are potential mitogens for epithelialization as well as fibroblasts (Pierce G F et al., J. Cell Biol., 109:429-440, 1989). In contrast, in the use of turmeric there is more selectivity with respect to mitogenicity. In smooth muscle cell research, rabbit smooth muscle cells from the aorta have been shown to inhibit smooth muscle cell proliferation (Huang H-C et al., Eur. J. Pharmacol., 221:381-384, 1992).

The route of intake of a drug is also very important. The advantage of using a drug topically as well as taking it orally would be that one is addressing the problem in two ways. Turmeric has been shown to increase HDL in comparison to LDL and hence may also be used in influencing the capillary system by altering the lipid content of blood. Very little of turmeric is systemically absorbed and hence may be working as an advantage by reducing the cholesterol in the blood and hence altering the patency of the vasculature.

The need to address the problem of skin ulcers is apparent. No current animal model, single factor or drug exists (Rasmussen L H et al, Ann. Surg, 216:684-691, 1992). The literature has stressed more on carcinogenic, inflammatory metabolic modulatory or the oxidation properties of turmeric but no one has used this agent singly for wound healing. The present inventors are the first ones to use turmeric topically and orally as a single agent modality for wound healing.

The turmeric can be used in the form of a powder, such as is obtained in a food store. It can be administered orally and/or topically directly to the wound. When oral administration is employed, either alone or in combination with topical administration, turmeric is orally administered in an amount of 0.1-2.5 mg/kg of body weight. When topical administration is employed, either alone or in combination with oral administration, the amount topically administered is 0.1-1.0 $gm/cm^2$ of wound surface. These dosage levels are daily dosages and such amounts can be administered all at once or in divided doses.

The turmeric powder can be orally ingested, for example with drinking water. The powder can also be directly administered topically to the wound.

The turmeric can be administered to mammals, including humans, to promote wound healing. Any type of wound on the outside surface of the body can be treated, for example, surgical wounds (such as incisions), ulcers, and any other injury to the body in which the skin or other tissue is broken, cut, pierced, torn, etc.

EXPERIMENTAL

Experiment 1

Thirty-two Sprague-Dawley rats (275 grams) were kept under NIH guidelines and fed water and rat chow ad libitum. Two weeks after procurement, each animal was anesthetized with ketamine (60 mg/kg) and xylazine (8 mg/kg) intramuscularly. A full thickness wound through the panniculus carnosus was then formed on the dorsal midline of each animal from a circular template 2.5 cm in diameter. Immediately after wounding, the animals were placed under a fixed camera (Nikon 8008S) and photographed. All wounds were left open to heal by secondary intention and the animals were randomly placed into one of four groups. The wounds in Group 1 animals were dressed daily with 0.9% normal saline (controls). Turmeric powder (Raja Foods, Lincolnwood, Ill.) was applied topically in an amount of 0.5 gm/cm$^2$ of wound surface to the wounds of Group 2 animals. In Group 3, turmeric powder was applied topically to the wounds and the animals were given a 1.5% turmeric aqueous suspension by mouth via daily drinking water. Group 4 animals were given 1.5% turmeric solution by mouth and their wounds were dressed daily with 0.9% normal saline. The area of each wound was calculated on days 0, 3, 6, 10, 17, 25, 28 and 32 and the mean wound size of each treatment group was compared to controls at each time interval. At days 0, 3, 6, and 10, the mean area of the wounds was similar in all groups. At days 17, and 25 however, the treatment groups exhibited significantly smaller wounds when compared to controls ($p<0.05$ each group). In addition, all animals in Groups 2 and 3 and 75% of the animals in Group 4 had healed wounds at day 32, compared to only 38% in the control group. Thus, turmeric powder, in both oral and topical applications, enhanced wound contraction and healing in this model. All of the wounds in this study exhibited the typical pattern of wound healing, with minimal wound contraction noted during the initial lag phase followed by a rapid increase in wound contraction during the proliferative phase (day 6 to day 25) (Li C J et al., *Proc. Natl. Acad. Sci. USA*, 90:1839–1842, 1993). In the animals treated with local and/or oral turmeric the mean wound sizes were significantly smaller during this proliferative phase when compared to the mean wound size of the animals treated with normal saline. This indicates that local application and oral intake of turmeric enhances wound contraction when compared to daily cleansing with saline.

Case Histories

Both of the following patients were suffering from refractive chronic ulcer of the leg.

Case History #1

H. W., a 60 year old male construction worker who smokes 5 cigarettes a day, drinks; weekends nearly a pint of gin. He presented complaining of 3 weeks ago hitting his left shin on the cement mixer at work resulting with an open wound. He came to be seen in the emergency room one week after the accident when the wound became inflamed. His past history is not significant to any major ailments. He was treated with split thickness skin graft 20 years ago. On examination, there was an open wound over the left lateral malleolus 2 cm×1 cm and was tender, x-rays showed no fracture. Wet to dry dressing was used. Initially, he was treated with antibiotic, viz, Keflex.

After 3 months, the ulcer over the left lateral malleolus increased in size to 3.4 cm×1.7 cm. At this time the patient was started on IRB approved protocol using turmeric as a local wound dressing and leg elevation.

Two weeks later the patient was seen and his ulcer was unchanged, but dermatitis was present. His treatment was continued but, compressing wrapping was held due to dermatitis. Two weeks later his ulcer was smaller and over the next three months with the therapy of turmeric, supportive bandage and skin elevation, his ulcer completely healed.

| Wound site measurements: | |
| --- | --- |
| Day 1 (when measurement above was taken) | 3.4 × 1.7 cm |
| Day 8 | 3.0 × 1.8 cm |
| Day 12 | 3.0 × 1.8 cm |
| Day 15 | 3.0 × 1.5 cm |
| Day 22 | 3.0 × 1.7 cm |
| Day 54 | 2.0 × 1.7 cm |
| Day 97 | 1.0 × 2.0 cm |
| Day 107 | 1.0 × 1.0 cm |
| Day 118 | wound epithelialized |

Case History #2

C. G. is a 25 year old male who one year ago fell and fractured his right rib with resulting pneumothorax. Post operatively he developed deep venous thrombosis in the right skin, treated with IV heparin and placed on Coumadin. Ascending venogram showed obstruction at the right saphenofemoral junction. He underwent a Linto Operation. He was referred complaining of chronic ulcer on the right skin over the anterior lateral aspect lower third since the injury. Initially, he was treated by skin grafts four times which all broke down. On examination, an otherwise healthy individual had an edematous right leg and foot. The ulcer was 3 cm×3 cm which was diagnosed as chronic venous stasis ulcer. Both dorsal and pedal pulses were palpable. After failure of the last skin graft, a microvascular flap was attempted but on the operating table it was found that he had high venous pressure so a free flap was not done. Instead a fascio-cutaneous flap was used to cover the defect and a split thickness skin graft was put on to cover the secondary defect. Unfortunately these wounds soon broke down resulting in a skin ulcer. The patient had a skin graft with a venous element associated with it. His wound deteriorated and reached a maximum size of 6×9 cm. A lateral arm free flap was contemplated, but not done due to high venous pressure.

Day 1: Started initial turmeric treatment. The right leg ulcer was measured as 5.5 cm×1 cm.

Day 15: Red granulation tissue was observed and the ulcer reduced in size to 4.5 cm×9 mm.

Day 87: The size of the ulcer was 3 cm×5 mm.

Day 121: The skin ulcer of the leg was completely healed.

Day 175: The skin ulcer remained healed.

Experiment 2

In vitro analysis of the effect of turmeric on the endothelial cells from human umbilical cord.

This pilot experiment was undertaken to assess the effects of turmeric powder on cultured endothelial cells. Human umbilical cords were obtained and the umbilical vein was harvested by microsurgical technique. The vein was then sectioned into 4 mm segments and cultured in Trypsin-EDTA solution for one hour. The culture fluid was centrifuged and the supernatant collected. Following this the tissue was recultured for one and a half hours and centrifuged. The supernatant was then pooled with the supernatant previously collected and this fluid was centrifuged. The resultant pellet was resuspended in 10 ml volume of. Eagles-MEM with 10% fetal calf serum. Penicillin, streptomycin and fungizone were included in the solution. The cell suspension was then added in 100 microliter aliquots to a 96 flat bottom cell plate. Various concentrations of turmeric were added to the cell plates and this plate was incubated in 95% oxygen, 5% carbon dioxide air at 37 degrees Celsius for 72 hrs. Following incubation the cells were pulsed 16 hrs with tritiated thymidine and then harvested onto filter paper disk for counting by liquid scintillation. Cell counts revealed that cells cultured in media alone resulted in <500 CPM (counts per minute) whereas those cells cultured in media as well as turmeric [0.01%] resulted in 4900 CPM (counts per minute). These results demonstrate an in vitro proliferative effect of turmeric on endothelial cells isolated from umbilical vein.

We claim:

1. A method of promoting healing of a wound in a patient, which consists essentially of administering a wound-healing agent consisting of an effective amount of turmeric powder to said patient.

2. The method according to claim 1, wherein said turmeric is orally administered to said patient.

3. The method according to claim 1, wherein said turmeric is topically administered to said patient.

4. The method according to claim 1, wherein said turmeric is both orally and topically administered to said patient.

5. The method according to claim 1, wherein said wound is a surgical wound.

6. The method according to claim 1, wherein said wound is a body ulcer.

* * * * *

REEXAMINATION CERTIFICATE (3500th)
United States Patent [19]
Das et al.

[11] B1 5,401,504
[45] Certificate Issued Apr. 21, 1998

[54] USE OF TUMERIC IN WOUND HEALING

[75] Inventors: Suman K. Das; Hari har P. Cohly, both of Jackson, Miss.

[73] Assignee: The University of Mississippi Medical Center, Jackson, Miss.

Reexamination Request:
No. 90/004,433, Oct. 28, 1996

Reexamination Certificate for:
Patent No.: 5,401,504
Issued: Mar. 28, 1995
Appl. No.: 174,363
Filed: Dec. 28, 1993

[51] Int. Cl.$^6$ .................................................. A61K 35/78
[52] U.S. Cl. ..................... 424/195.1; 514/925; 514/926; 514/927; 514/928
[58] Field of Search .................. 424/195.1; 514/925, 514/926, 927

[56] References Cited

PUBLICATIONS

Gujral et al., Journal of Indian Medical Association, vol. XXII, No. 7, pp. 273–276, 1953.
Frawley, "Ayurvedic Healings", pp. 221–223 1989.
"The Wealth of India", pp. 401–405 1950.
"Indian Materia Medica", pp. 414–418 1976.
"Economic and Medicinal Plant Research", vol. 4, pp. 149–151 1990.
Sivananda, "Home Remedies", pp. 233–235 1958.
"The Ayurvedic Pharmacopoeia of India", pp. 45–46 1986.
"Selected Medicinal Plants of India", p. 56 1992.
"Indian Medicinal Plants Used in Ayurvedic Preparation", pp. 121–124 1980.
Srimal, "Haldi Can Heal", Science Today, pp. 26–27 1986.
Rastogi et al., "A Compendium of Indian Medicinal Plants", vol. 57, 1985–1989 1993.
Ray et al., "Susruta Samhita", p. 62 1980.
Amman et al., "Pharmacology of Cuecum longa", Plant Med. vol. 57, pp. 1–6 1991.
Amman et al., "Curcumin: A Potent Inhibitor of Leukotriene B4 Formation" 1992.
Srinivas et al., Archives of Biochemistry and Biophysics, vol. 292, No. 2, pp. 617–623 Feb. 1, 1991.
Jain, "Dictionary of Indian Folk Medicine and Ethnobotany", pp. 65–66 1991.
Asolkar et al., Second Supplement to Glossary Of Indian Medicinal Plants With Active Principles Part I(A–K), (1965–1981), pp. 246–247 1992.
Shalini et al., Molecular and Cellular Biochemistry, vol. 95 pp. 21–30 1990.
Srinivasan et al., Free Radical Biology and Medicine, vol. 11, pp. 277–283 1991.
Sharma, "Dravyaguna–Vijana vol. II(Vegetable Drugs)", pp. 162–164 1984.
"Chaukhambha Orientalia", section 332 1979.
"rajnighantu of Pandit Narahari", pp. 174–175 1939.
"Bhavaprakasha", p. 115 1969.
Sharma, "Ayurveda Ka Vaijnanika Itihasa", p. 187 1975.
Chauhan, "Kya Khain Aur Kyuon", p. 157 1979.
Sattar, "Bustanul Mufredat", p. 252 1867.
Satry, "Prayogatmak Abhinav Dravyaguna Vigyanam", pp. 354–356 1991.
Kabiruddin, "Makhzanul Mufredat vol. II", pp. 207–208 1955.
Khan, "Khazanatul Adviya vol.–3", pp. 909–910 1920.
Dhawan, Indian Spices, vol. 30, No. 283, 19–20 1993.
Reddy et al., Am. Nutrition Metals 1992.
Dey, "Indian Medicinal Plants", p. 157 1988.

*Primary Examiner*—Shailendra Kumar

[57] ABSTRACT

Method of promoting healing of a wound by administering turmeric to a patient afflicted with the wound.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–6 are cancelled.

* * * * *